(12) United States Patent
Kim (10) Patent No.: US 11,786,572 B2
(45) Date of Patent: Oct. 17, 2023

(54) COMPOSITION FOR PREVENTING OR TREATING OSTEOPOROSIS

(71) Applicants: PENS CO., LTD., Seoul (KR); Hong Sik Kim, Goyang-si (KR)

(72) Inventor: Hong Sik Kim, Goyang-si (KR)

(73) Assignees: PENS CO., LTD., Seoul (KR); Hong Sik Kim, Goyang si (KR)

( * ) Notice: Subject to any disclaimer, the term of this patent is extended or adjusted under 35 U.S.C. 154(b) by 0 days.

(21) Appl. No.: 17/566,408

(22) Filed: Dec. 30, 2021

(65) Prior Publication Data

US 2022/0118039 A1    Apr. 21, 2022

Related U.S. Application Data

(62) Division of application No. 16/976,367, filed as application No. PCT/KR2019/012105 on Sep. 19, 2019, now abandoned.

(30) Foreign Application Priority Data

Apr. 29, 2019  (KR) .................. 10-2019-0049946

(51) Int. Cl.
| | | |
|---|---|---|
| *A61K 36/515* | (2006.01) | |
| *A61P 19/10* | (2006.01) | |
| *A61K 36/35* | (2006.01) | |

(52) U.S. Cl.
CPC ............ *A61K 36/515* (2013.01); *A61K 36/35* (2013.01); *A61P 19/10* (2018.01); *A61K 2236/331* (2013.01); *A61K 2236/37* (2013.01)

(58) Field of Classification Search
None
See application file for complete search history.

(56) References Cited

U.S. PATENT DOCUMENTS

| | | |
|---|---|---|
| 7,074,435 B2 | 7/2006 | Cho et al. |
| 2017/0095539 A1 | 4/2017 | Tan |
| 2017/0368127 A1 | 12/2017 | Yang et al. |

FOREIGN PATENT DOCUMENTS

| | | | |
|---|---|---|---|
| CN | 1260984 A | | 7/2000 |
| CN | 101773490 A | * | 7/2010 |
| CN | 104147409 A | | 11/2014 |
| CN | 105311473 A | | 2/2016 |
| CN | 105412569 A | | 3/2016 |
| CN | 107569657 A | | 1/2018 |
| JP | 07-101868 A | | 4/1995 |
| JP | 2005-281221 A | | 10/2005 |
| JP | 2005281221 A | * | 10/2005 |
| KR | 10-2005-0007716 A | | 1/2005 |
| KR | 10-1607545 B1 | | 3/2016 |
| KR | 10-2017-0054115 A | | 5/2017 |
| KR | 10-1783119 B1 | | 9/2017 |

OTHER PUBLICATIONS

International Search Report for PCT/KR2019/012105 dated Jan. 10, 2020 [PCT/ISA/210].
Written Opinion for PCT/KR2019/012105 dated Jan. 10, 2020 [PCT/ISA/237].

* cited by examiner

*Primary Examiner* — Susan Hoffman
(74) *Attorney, Agent, or Firm* — Sughrue Mion, PLLC (57) ABSTRACT

A composition for preventing or treating osteoporosis, contains a *Gentiana scabra* extract and a *Sambucus williamsii* extract. The composition for preventing or treating osteoporosis is capable of increasing bone formation and inhibiting bone resorption. In addition, the composition increases bioaffinity and has no side effects by containing a *Gentiana scabra* extract and a *Sambucus williamsii* extract, which are natural products, thereby stably exhibiting an effect of preventing or treating osteoporosis.

6 Claims, 7 Drawing Sheets

Specification includes a Sequence Listing.

```
                         SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: GAPDH Primer F

<400> SEQUENCE: 1
atggaaatcc catcaccatc t                                          21

<210> SEQ ID NO 2
<211> LENGTH: 18
<212> TYPE: DNA
<213> ORGANISM: Artificial Sequence
<220> FEATURE:
<223> OTHER INFORMATION: GAPDH Primer R

<400> SEQUENCE: 2
cgccccactt gattttgg                                              18

<210> SEQ ID NO 3
<211> LENGTH: 20
<212> TYPE: DNA
<213> ORGANISM: Artificial Sequence
<220> FEATURE:
<223> OTHER INFORMATION: ALP Primer F

<400> SEQUENCE: 3
ccgctttaac cagtgcaaca                                            20

<210> SEQ ID NO 4
<211> LENGTH: 20
<212> TYPE: DNA
<213> ORGANISM: Artificial Sequence
<220> FEATURE:
<223> OTHER INFORMATION: ALP Primer R

<400> SEQUENCE: 4
cccgattcat cacggagatg                                            20

<210> SEQ ID NO 5
<211> LENGTH: 18
<212> TYPE: DNA
<213> ORGANISM: Artificial Sequence
<220> FEATURE:
<223> OTHER INFORMATION: Osteocalcin Primer F
```

```
<400> SEQUENCE: 5
caggagggca gcgaggta                                              18

<210> SEQ ID NO 6
<211> LENGTH: 19
<212> TYPE: DNA
<213> ORGANISM: Artificial Sequence
<220> FEATURE:
<223> OTHER INFORMATION: Osteocalcin Primer R

<400> SEQUENCE: 6
gctcccagcc attgataca                                             19

<210> SEQ ID NO 7
<211> LENGTH: 19
<212> TYPE: DNA
<213> ORGANISM: Artificial Sequence
<220> FEATURE:
<223> OTHER INFORMATION: NFATC-1 Primer F

<400> SEQUENCE: 7
tggcctcccg cttatctct                                             19

<210> SEQ ID NO 8
<211> LENGTH: 20
<212> TYPE: DNA
<213> ORGANISM: Artificial Sequence
<220> FEATURE:
<223> OTHER INFORMATION: NFATC-1 Primer R

<400> SEQUENCE: 8
ggataacgca ggcgaattgt                                            20

<210> SEQ ID NO 9
<211> LENGTH: 24
<212> TYPE: DNA
<213> ORGANISM: Artificial Sequence
<220> FEATURE:
<223> OTHER INFORMATION: Cathepsin K Primer F

<400> SEQUENCE: 9
gataatgtga accatgcagt gttg                                       24

<210> SEQ ID NO 10
<211> LENGTH: 20
<212> TYPE: DNA
<213> ORGANISM: Artificial Sequence
<220> FEATURE:
<223> OTHER INFORMATION: Cathepsin K Primer R

<400> SEQUENCE: 10
ccagtgcttg cttcccttct                                            20

<210> SEQ ID NO 11
<211> LENGTH: 19
<212> TYPE: DNA
<213> ORGANISM: Artificial Sequence
<220> FEATURE:
<223> OTHER INFORMATION: MMP-9 Primer F

<400> SEQUENCE: 11
acgccacgca ttttcaaaa                                             19

<210> SEQ ID NO 12
<211> LENGTH: 18
```

```
<212> TYPE: DNA
<213> ORGANISM: Artificial Sequence
<220> FEATURE:
<223> OTHER INFORMATION: MMP-9 Primer R

<400> SEQUENCE: 12
ggcccattcc ctccacat                                              18
```

COMPOSITION FOR PREVENTING OR TREATING OSTEOPOROSIS

CROSS REFERENCE TO RELATED APPLICATIONS

This application is a Divisional application of U.S. application Ser. No. 16/976,367 filed Aug. 27, 2020, now abandoned, which is a National Stage of International Application No. PCT/KR2019/012105 filed Sep. 19, 2019, claiming priority based on Korean Patent Application No. 10-2019-0049946 filed Apr. 29, 2019.

SEQUENCE LISTING

The content of the electronically submitted sequence listing, file name: Sequence_Listing_As_Filed.txt; size: 2,761 bytes; and date of creation: Dec. 30, 2021, filed herewith, is incorporated herein by reference in its entirety.

TECHNICAL FIELD

The present invention relates to a composition for preventing or treating osteoporosis, comprising a *Gentiana scabra* extract and a *Sambucus williamsii* extract.

BACKGROUND ART

Bone metabolism disease is emerging as a major problem as we enter the aging society, and osteoporosis accounts for the largest proportion of bone metabolic diseases. On the other hand, osteoporosis is a disease in which the composition of the skeleton is changed due to the imbalance of calcium metabolism, thereby reducing bone mass and easily causing fractures of the radius, femoral, and vertebrae, and in particular has the highest incidence in post-menopausal women, and estrogen secretion has been reported as the main cause.

Bone remodeling continues to occur even after bone growth is over, homeostasis is maintained between bone formation by osteoblasts and bone resorption by osteoclasts through this process, and bone tissue under normal conditions has a balance of bone formation and bone resorption.

Osteoblast progenitor cells are differentiated by various factors (for example, BMP, ALP, and TGF-β) to transform into osteoblasts, and fully differentiated osteoblasts are present in the form of osteocytes in the bone matrix by non-protein and protein components. On the other hand, osteoblasts produce a receptor activator of NK-kB ligand (RANKL) and its induction receptor (decoy receptor), OPG (osteoprotegerin).

A very important process for bone resorption is differentiation into osteoclasts, and the main ligand that mediates differentiation is RANKL, and when RANKL binds to RANK, which is a receptor on the surface of osteoclast progenitor cells, osteoclast progenitor cells mature into osteoclasts, resulting in bone resorption. In addition, genes that play an essential role in osteoclast differentiation are substances such as NF-kB and c-FOS.

However, If OPG (osteoprotegerin) is combined with RANKL, the binding between RANKL and RANK is blocked, and thus, the formation of osteoclasts is inhibited and more bone resorption than necessary does not occur. Resorption or destruction of old bones is caused by osteoclasts produced from blood cells (hematopoietic stem cells), and are used to maintain body function by forming holes in the bone and releasing a small amount of calcium into the bloodstream. On the other hand, osteoblasts produced from bone cells fill the holes with collagen and cover the deposits (hydroxyapatite) of calcium and phosphorus to rebuild the skeleton by making new hard bones.

It takes about 100 days for the bones to begin to break down and be remodeled again into new bones. In infants, bone calcium changes 100% in a year, but in adults, about 10-30% of the skeleton is remodeled through this process every year, and the osteoclastic rate and the osteoblastic rate must be the same to maintain the same bone density as before. When the balance is broken in such an important bone, many diseases may be caused, in particular, osteoporosis is a representative disease.

As a known treatment method of osteoporosis, there are estrogen therapy, calcitonin therapy, calcium supplements, vitamin D derivative therapy, and so on, and estrogen therapy and calcitonin therapy have been reported as the most commonly used treatment methods, but they have been reported to have various side effects and disadvantages that are difficult to control when to administer. For this reason, in recent years, studies have been conducted to treat osteoporosis by developing a natural product with no side effects and low cost.

Accordingly, as a prior art using natural products, Korean Patent Laying-Open No. 10-2017-0054115 discloses a pharmaceutical composition for preventing or treating osteoporosis comprising an extract from germinated gemmule of bean, and Korea Patent No. 10-178311 discloses a composition for preventing or treating bone metabolic diseases, comprising the combined extracts of *Schisandra chinensis*, *Eucommia ulmoides*, and *Lycium barbarum* as active ingredients.

However, the above-mentioned prior arts shows that the proliferation and differentiation ability of osteoblasts or the expression of factors related to osteoblasts may be increased by using natural products, but since they do not disclose the effect on bone resorption by osteoclasts, it is necessary to develop a therapeutic agent for osteoporosis of a new natural material capable of maintaining homeostasis of bone formation and bone resorption.

DISCLOSURE

Technical Problem

In order to solve the above-mentioned problems, it is an object of the present invention to provide a composition for preventing or treating osteoporosis, which is capable of increasing bone formation and inhibiting bone resorption.

In addition, it is another object of the present invention to provide a composition for preventing or treating osteoporosis, which increases bioaffinity and has no side effects by comprising a *Gentiana scabra* extract and a *Sambucus williamsii* extract, which are natural products, thereby stably exhibiting an effect of preventing or treating osteoporosis.

Technical Solution

The present invention provides a composition for preventing or treating osteoporosis, comprising a *Gentiana scabra* extract and a *Sambucus williamsii* extract, according to an embodiment of the present invention.

The mixing weight ratio of the *Gentiana scabra* extract and the *Sambucus williamsii* extract may be 1:0.1 to 10.

The composition may comprise the *Gentiana scabra* extract and the *Sambucus* williamsii extract in an amount of 0.001 to 100% by weight, based on the total weight of the total composition.

The *Gentiana scabra* extract and the *Sambucus williamsii* extract may be extracted by hot water extraction.

The composition may improve expression of a gene related to bone formation.

The gene related to bone formation may be one or more gene selected from the group consisting of ALP, osteocalcin, BMP, TGF-β, and osteoprotegerin.

The composition may inhibit the expression of a gene related to bone resorption.

The gene related to bone resorption may be one or more gene selected from the group consisting of NF-kB, c-FOS, NFATC-1, Cathepsin K, and MMP-9.

The present invention provides a method of preparing a composition for preventing or treating osteoporosis, according to another embodiment of the present invention.

The method of preparing the composition may comprise the steps:

1) putting and heating *Gentiana scabra* and *Sambucus williamsii* in a solvent to obtain extracts; and 2) concentrating the extracts obtained from step 1) under reduced pressure.

The heating temperature in step 1) above may be 80 to 100° C.

Step 2) above may be carried out at 30 to 70° C.

Advantageous Effects

The composition for preventing or treating osteoporosis according to the present invention may provide an effect of increasing bone formation and inhibiting bone resorption.

In addition, the composition for preventing or treating osteoporosis according to the present invention may increase bioaffinity and have no side effects by comprising a *Gentiana scabra* extract and a *Sambucus williamsii* extract, which are natural products, as main ingredients, thereby stably providing an effect of preventing or treating osteoporosis.

BRIEF DESCRIPTION OF DRAWINGS

FIGS. 1a to 1e show the measured results of ALP activity according to the concentration of the extracts according to an embodiment of the present invention, wherein FIGS. 1a, 1b, 1c, 1d, and 1e show the results corresponding to Reference Example 1, Reference Example 2, Example 1, Example 2, and Example 3, respectively.

FIGS. 2a to 2e show the measured results of tartrate-resistant acid phosphate (TRAP) enzyme activity according to the concentration of the extracts according to an embodiment of the present invention, wherein FIGS. 2a, 2b, 2c, 2d, and 2e show the results corresponding to Reference Example 1, Reference Example 2, Example 1, Example 2, and Example 3, respectively.

FIGS. 3a to 3e show the measured results of the expression level of ALP gene according to the concentration of the extracts according to an embodiment of the present invention, wherein FIGS. 3a, 3b, 3c, 3d, and 3e show the results corresponding to Reference Example 1, Reference Example 2, Example 1, Example 2, and Example 3, respectively.

FIGS. 4a to 4e show the measured results of the expression level of osteocalcin gene according to the concentration of the extracts according to an embodiment of the present invention, wherein FIGS. 4a, 4b, 4c, 4d, and 4e show the results corresponding to Reference Example 1, Reference Example 2, Example 1, Example 2, and Example 3, respectively.

FIGS. 5a to 5e show the measured results of the expression level of NFATC-1 gene according to the concentration of the extracts according to an embodiment of the present invention, wherein FIGS. 5a, 5b, 5c, 5d, and 5e show the results corresponding to Reference Example 1, Reference Example 2, Example 1, Example 2, and Example 3, respectively.

FIGS. 6a to 6e show the measured results of the expression level of Cathepsin K gene according to the concentration of the extracts according to an embodiment of the present invention, wherein FIGS. 6a, 6b, 6c, 6d, and 6e show the results corresponding to Reference Example 1, Reference Example 2, Example 1, Example 2, and Example 3, respectively.

FIGS. 7a to 7e show the measured results of the expression level of MMP-9 gene according to the concentration of the extracts according to an embodiment of the present invention, wherein FIGS. 7a, 7b, 7c, 7d, and 7e show the results corresponding to Reference Example 1, Reference Example 2, Example 1, Example 2, and Example 3, respectively.

BEST MODE

In the present invention, the accompanying drawings may be illustrated with exaggerated expressions for distinction and clarity from the prior art, and for convenience of grasping the technology. In addition, the terms to be described later are terms defined in consideration of functions in the present invention and may vary according to a user's or operator's intention or practice, and thus, definitions of these terms will have to be made based on technical content throughout the present specification. On the other hand, the embodiments are only an exemplary matter of the components presented in the claims of the present invention and does not limit the scope of the present invention, and the scope of the invention should be interpreted based on the technical idea throughout the specification of the present invention.

The composition for preventing or treating osteoporosis according to an embodiment of the present invention comprises a *Gentiana scabra* extract and a *Sambucus williamsii* extract as active ingredients.

*Gentiana scabra* used in the present invention, which is *Gentiana scabra* Bunge var. *buergeri* (Miguel) Maxim, is mainly distributed in Korea, Japan, northeastern China, and eastern Siberia, and it is a herbaceous perennial plant belonging to Gentianaceae, Gentianales, Gamopetalous, Eudicots, and grows on the grass in the mountains. In addition, it has the effect of quenching the exuberant fire of the liver and gall bladder as the known efficacy and effects, is used as an agent for eliminating damp-heat, an agent for quenching the fire of the liver and gall bladder, a bitter stomachic, and a cholagogue, and is effective in digestion, hyperfunction of the liver, and anti-inflammatory.

The present inventors confirmed the effect of promoting bone formation and inhibiting bone resorption as a new effect of *Gentiana scabra*, and confirmed that *Gentiana scabra* may be effectively used for preventing or treating osteoporosis among bone metabolic diseases.

In general, it is known that *Gentiana scabra* is effective for a strong stomach, sores with swelling, scabies, epilepsy, night sweat, convulsions, roundworm, heart disease, eczema, gastritis, chlorhydria, hypochlorhydria, gastric catarrh, and gastrosia, but it was first confirmed by the present inventors that it is effective in preventing or treating osteoporosis in connection with bone metabolic disease.

In one embodiment of the present invention, the *Gentiana scabra* may be a leaf, a sprout, a stem, or a root of the *Gentiana scabra*, but is not limited thereto. It is preferably a root.

*Sambucus williamsii* used in the present invention is a summergreen shrub belonging to *Sambucus* and has the efficacy of removing pain by activating blood flow, and thus, it is effective for wind-dampness type arthritis, low back pain, fracture, and traumatic hemorrhage, and is mainly used for the elimination of postpartum hematostasis and bruising.

The present inventors have confirmed that since the *Sambucus williamsii* may promote bone formation and inhibit bone resorption, it may be effectively used for preventing or treating osteoporosis among bone metabolic diseases.

In the present invention, the term "preventing" refers to all actions that inhibit or delay the onset of osteoporosis through administration of the composition.

In the present invention, the term "treating" refers to all actions that improve or beneficially alter the symptoms caused by osteoporosis through administration of the composition.

In one embodiment of the present invention, the extract may be obtained by any one or more methods selected from a solvent extraction method, an ultrasonic extraction method, a supercritical extraction method, and an extraction method by a fermentation method and a foaming method, but is not limited thereto. The solvent extraction method is characterized by using water, a lower alcohol of $C_1$ to $C_4$, or a mixed solvent thereof.

In the present invention, as the extraction method, the solvent extraction method is preferably used, and a solvent extraction method using hot water is more preferably used, but is not limited thereto.

Wherein the solvent extraction method using hot water may not only safely extract the active ingredients contained in the natural product, but also extracting without using compounds, thereby reducing the side effects that may result from the final product or composition and increasing bioaffinity.

The mixing weight ratio of the *Gentiana scabra* extract and the *Sambucus williamsii* extract may be 1:0.1 to 10, preferably 1:0.4 to 2.5, but is not limited thereto. Wherein, when the mixing weight ratio is 1:0.1 to 10, the improvement effect on bone formation and the inhibition effect on bone resorption may be balanced with each other.

The *Gentiana scabra* extract and the *Sambucus williamsii* extract may be included in an amount of 0.001 to 100% by weight, preferably 0.001 to 50% by weight, more preferably 0.001 to 20% by weight, based on the total weight of the total composition, but is not limited thereto. If the content of the extracts is less than 0.001% by weight based on the total composition, the concentration may be too low to sufficiently have an effect of inducing bone formation and inhibiting bone resorption.

The *Gentiana scabra* extract may be included in an amount of 0.001 to 99.999% by weight, preferably 0.001 to 80% by weight, more preferably 30 to 70% by weight, based on the total composition, but is not limited thereto.

The *Sambucus williamsii* extract may be included in an amount of 0.001 to 99.999% by weight, preferably 0.001 to 80% by weight, more preferably 30 to 70% by weight, but is not limited thereto.

The composition may improve the expression of a gene related to bone formation, wherein the expression of the gene means that it occurs together in the process that osteoblast progenitor cells are differentiated into osteoblasts or in the process that osteoblasts are changed to the osteocyte form, and wherein the gene may be one or more genes selected from the group consisting of ALP, osteocalcin, BMP, TGF-β, and osteoprotegerin, preferably ALP and osteocalcin, which are the most important factors in the process that osteoblast progenitor cells are differentiated into osteoblasts, but is not limited thereto.

The ALP is a gene that is present in bone tissue and is known to increase its activity when bone growth is actively occurring.

The osteocalcin refers to a protein that is synthesized by osteoblasts during bone remodeling and is bound to the extracellular matrix of bone.

In addition, the composition may inhibit the expression of a gene related to bone resorption, wherein the expression of the gene means that it occurs together in the process of differentiation into osteoclasts. Wherein the gene may be one or more genes selected from the group consisting of NF-kB, c-FOS, NFATC-1, Cathepsin K, and MMP-9, preferably is one or more genes selected from the group consisting of NFATC-1, Cathepsin K, and MMP-9, but is not limited to.

Wherein NFATC-1 is a gene whose expression increases in the differentiation process of osteoclasts, whereas Cathepsin K and MMP-9 are genes whose expression level increases when the differentiation process of osteoclasts continues.

The composition of the present invention may be used as a pharmaceutical composition, and may further comprises one or more additives selected from the group consisting of pharmaceutically acceptable carriers, excipients, and diluents. As such, the kind and amount of additives that are further included in the pharmaceutical composition of the present invention are according to those generally known in the related art.

The composition of the present invention may comprise a pharmaceutically acceptable carrier. The composition comprising a pharmaceutically acceptable carrier may be various formulations, oral or parenteral. It is prepared using diluents or excipients, such as a filler, an extender, a binder, a wetting agent, a disintegrating agent, a surfactant, and so on, which are usually used when formulated. Solid formulations for oral administration include a tablet, a pill, a powder, a granule, a capsule, and so on, and such solid formulations are prepared by mixing at least one excipient, for example, starch, calcium carbonate, sucrose or lactose, gelatin, and so on with one or more compounds. In addition to simple excipients, lubricants such as magnesium stearate, talc, and so on are also used. Liquid formulations for oral administration include a suspension, a solution for internal use, an emulsion, a syrup, and so on, and may include various excipients, such as a wetting agent, a sweetener, a flavoring agent, a preservative, and so on, in addition to commonly used simple diluents such as water and liquid paraffin. Formulations for parenteral administration include a sterile aqueous solution, a non-aqueous solvent, a suspension, an emulsion, a lyophilized formulation, and a suppository. As the non-aqueous solvent and the suspension solvent, propylene glycol, polyethylene glycol, vegetable oils such as olive oil, injectable esters such as ethyl oleate, and so on may be used. As a base for suppositories, witepsol, macrogol, Tween 61, cacao butter, laurin butter, glycerogelatin, and so on may be used.

The composition of the present invention may be used by formulating appropriately for the application form in the form of an oral administration agent such as a tablet, a pill, a powder, a granule, a capsule, a suspension, a solution for internal use, an emulsion, a syrup, and so on; and a parenteral administration agent such as an aqueous solution as a sterile injectable solution, a non-aqueous solvent, a suspension, and an emulsion, a lyophilized formulation, or a suppository, and so on.

The composition may be administered through any general route, as long as it can reach a target tissue. The composition of the present invention may be injected by intraperitoneal administration, intravenous administration, intraarterial administration, intramuscular administration, intraosseous administration, intrauterine administration, intrathecal administration, subcutaneous administration, intradermal administration, oral administration, intranasal administration, intrapulmonary administration, intrarectal administration, intracerebroventricular administration, as desired, but is not limited thereto. In addition, the composition may be administered by any device capable of transporting the active substance to a target cell.

The composition of the present invention may be administered in a pharmaceutically effective amount.

In the present invention, the term "a pharmaceutically effective amount" refers to an amount sufficient to treat a disease at a reasonable benefit/risk ratio applicable to medical treatment, and the effective dose level may be determined depending on the factors including the kind and severity of individuals, age, sex, and the type of virus to be infected, the activity of the drug, the sensitivity to the drug, the time of administration, the route of administration and the rate of excretion, the duration of treatment, the drugs used simultaneously, and other factors well known in the medical field.

For example, the composition of the present invention may be administered in an amount of 0.01 g to 20 g per day based on the mixed dosage of *Gentiana scabra* and *Sambucus williamsiis*. Specifically, in the case of an extract, an extract prepared using *Gentiana scabra* and *Sambucus williamsiis* in the above content range may be considered as a daily dosage.

The composition of the present invention may be administered as an individual therapeutic agent or may be administered in combination with other therapeutic agents, and may be administered sequentially or simultaneously with conventional therapeutic agents. In addition, it may be administered single or multiple times. Considering all of the above factors, it is important to administer an amount that can achieve the maximum effect in a minimal amount without side effects, and can be easily determined by those skilled in the art.

The composition of the present invention may be used alone or in combination with methods using surgery, hormonal therapy, drug therapy, and biological response modifiers, in order to prevent or treat osteoporosis.

In another embodiment, the present invention provides a food composition for preventing or improving osteoporosis, comprising a *Gentiana scabra* extract and a *Sambucus williamsii* extract as active ingredients.

Wherein the *Gentiana scabra* extract and the *Sambucus williamsii* extract are the same as described above.

The *Gentiana scabra* extract and the *Sambucus williamsii* extract may be prepared and intaked in the form of food that can be eaten all the time and improve osteoporosis. Wherein the content of the *Gentiana scabra* extract and the *Sambucus williamsii* extract to be contained in the food is not particularly limited, but may be included as an example, in an amount of 0.001 to 100% by weight based on the total weight of the food composition. When the food is a beverage, they may be included as an example, in a ratio of 0.01 to 60 g, and as another example, in a ration of 0.1 to 60 g, based on 100 ml.

In addition, the composition may include additional ingredients that may be commonly used in food compositions to improve odor, taste, visual sense, and so on. For example, it may include vitamin A, D, E, B1, B2, B6, B12, niacin, biotin, folate, pantotenic acid, and so on. In addition, it may include minerals such as zinc (Zn), iron (Fe), calcium (Ca), chromium (Cr), magnesium (Mg), manganese (Mn), copper (Cu), and so on. In addition, it may include amino acids such as lysine, tryptophan, cysteine, valine, and so on. In addition, food additives such as preservatives (potassium sorbate, sodium benzoate, salicylic acid, sodium dehydroacetate, and so on), bactericides (bleaching powder and higher bleaching powder, sodium hypochlorite, and so on), antioxidants (butylhydroxyanisole (BHA), butylhydroxytoluene (BHT), and so on), colorants (tar pigment, and so on), color couplers (sodium nitrite, and so on), bleaching agents (sodium sulfite), seasoning agents (MSG sodium glutamate, and so on), sweetening agents (dulcin, cyclamate, saccharin, sodium, and so on), flavoring agents (vanillin, lactones, and so on), leavening agents (alum, D-potassium hydrogen tartrate, and so on), fortified dietary supplements, emulsifying agents, thickeners (paste), coating agents, gum base, foam inhibitors, solvents, improving agents, and so on may be added. The additives are selected according to the kind of food and used in an appropriate amount.

On the other hand, functional food for improving osteoporosis may be prepared using the *Gentiana scabra* extract and the *Sambucus williamsii* extract.

As a specific example, a processed food capable of improving osteoporosis may be prepared using the food composition, and, for example, may be prepared as a functional food in the form of confectionery, beverages, alcoholic beverages, fermented foods, canned foods, milk processed foods, meat processed foods, or noodles processed foods. Wherein the confectionery includes biscuits, pies, cakes, bread, candy, jelly, chewing gum, cereals (including meal replacement products such as cereal flakes, and so on), and so on. The beverages include drinking water, carbonated beverages, functional sports drinks, juices (for example, apple, pear, grape, aloe, tangerine, peach, carrot, tomato juices, and so ons), Sikhye (sweet rice drink), and so on. The alcoholic beverages include clear rice wine, whiskey, Soju (distilled spirits), beer, liquor, fruit wine, and so on. The fermented foods include soy sauce, soybean paste, red chili paste, and so on. The canned foods include canned seafoods (for example, canned tuna, canned mackerel, canned saury, canned top shell, and so on), canned meats (for example, canned beef, canned pork, canned chicken, canned turkey, and so on), and canned produce (for example, canned corn, canned peach, canned pineapple, and so on). The milk processed foods include cheese, butter, yogurt, and so on. The meat processed foods include pork cutlet, beef cutlet, chicken cutlet, sausage, sweet and sour pork, nuggets, Neobiani (marinated grilled beef slices), and so on. Noodles processed foods include dried noodles, thin noodles, instant noodles, udong noodles, Naengmyeon (cold noodles), seal packed wet noodles, and so on. In addition to these, the composition may be used for retort foods, soups, and so on.

The term "functional food" in the present invention is the same term as food for special health use (FoSHU), and refers to food with high medical and clinical effects, which is processed to efficiently exhibit the biological control function in addition to nutrition supply, wherein the food may be prepared in various forms such as tablets, capsules, powders, granules, liquids, pills, and so on, in order to obtain useful effects in improving osteoporosis.

According to another embodiment of the present invention, the present invention may provide a method of preparing a composition for preventing or treating osteoporosis.

The method of preparing the composition comprises the steps:

1) putting and heating *Gentiana scabra* and *Sambucus williamsii* in a solvent to obtain extracts; and 2) concentrating the extracts obtained from step 1) under reduced pressure.

Step 1) above is a step for extracting the active ingredients of the *Gentiana scabra* and the *Sambucus williamsiis*, and is a step of effectively extracting the active ingredients by heating the *Gentiana scabra* and the *Sambucus williamsiis* with a solvent extraction method. By way of an example, it may be a step of putting and heating the *Gentiana scabra* and the *Sambucus williamsii* in water, respectively.

The heating temperature in step 1) above may be 80 to 100° C. If the heating temperature is carried out at 80 to 100° C., it is possible to prevent the active ingredients from volatilizing or vaporizing during the execution while quickly extracting the active ingredients.

Step 2) above is a step of concentrating each of the *Gentiana scabra* extract and the *Sambucus williamsii* extract obtained from step 1) above under reduced pressure.

At this time, step 2) above may be carried out at 30 to 70° C., when concentrated in its temperature range, it is possible to reduce the concentration time.

The method of preparing a composition for preventing or treating osteoporosis, after step 2) above, may further comprise the steps of:

3) lyophilizing the concentrated extracts obtained from step 2) above; and 4) mixing the *Gentiana scabra* extract and the *Sambucus williamsii* extract obtained in powder form from step 3) above.

Step 3) above is a step of lyophilizing the concentrated extracts from step 2) above, and the *Gentiana scabra* extract and the *Sambucus williamsii* extract may be obtained in powder form through this step.

Then, step 4) above is a step of obtaining a mixture of the *Gentiana scabra* extract and the *Sambucus williamsii* extract, and may be easily changed by those skilled in the art.

MODE FOR CARRYING OUT THE INVENTION

Hereinafter, preferred embodiments of the present invention will be described.

However, embodiments of the present invention may be modified in various other forms, and the scope of the present invention is not limited to the embodiments described below. In addition, embodiments of the present invention are provided to more fully describe the present invention to those skilled in the art.

Preparation Example 1. Preparation of *Gentiana scabra* and *Sambucus williamsii* Extracts In order to prepare a *Gentiana scabra* extract and a *Sambucus williamsii* extract, 2 L of distilled water was placed into each 100 g of the original and hot water extraction was carried out at 90° C. for 5 hours. The filtered extract solutions were concentrated under reduced pressure at 50° C. to obtain samples in powder form through lyophilization. The yields of the *Gentiana scabra* extract and the *Sambucus williamsii* extract were 15.4% and 9.27%, respectively.

EXAMPLES

Examples were prepared as listed in Table 1 below, and the *Gentiana scabra* extract and the *Sambucus williamsii* extract as described in Table 1 were prepared according to Preparation Example 1 above.

TABLE 1

| Classification | Examples |
| --- | --- |
| Reference Example 1 | *Gentiana scabra* extract |
| Reference Example 2 | *Sambucus williamsii* extract |
| Example 1 | Extract of *Gentiana scabra* extract and *Sambucus williamsii* extract mixed at 7:3 |
| Example 2 | Extract of *Gentiana scabra* extract and *Sambucus williamsii* extract mixed at 5:5 |
| Example 3 | Extract of *Gentiana scabra* extract and *Sambucus williamsii* extract mixed at 3:7 |

Experimental Example 1. Cytotoxicity Evaluation

In this experimental example, an experiment was carried out to confirm the effect on the cytotoxicity when treated with the *Sambucus williamsii* extract and the *Gentiana scabra* extract of the present invention.

$1\times10^4$ MC3T3-L1 cells were seeded into a 96-well plate, and DMEM containing 10% FBS was used as the culture medium. After incubation for 12 hours, each extract (Examples 1 to 5) was treated at 100-1000 µg/ml and incubated for 24 hours. Then, 20 µl of WST reagent was added thereto, light was blocked with foil to minimize WST reduction by light, and the reaction was carried out for 3 hours. Optical density was measured at a wavelength of 560 nm using an iMARK™ Microplate Reader (Bio-Rad Laboratories Headquarters, Hercules, Calif., USA).

The obtained results of the cytotoxicity for each extract with $ED_{50}$ (which is a concentration at which cell viability is 50%) are shown in Table 2 below. As a result, it was shown that the *Gentiana scabra* extract and the *Sambucus williamsii* extract of the present invention is safe even at a high concentration of 600 µg/ml or more.

TABLE 2

| Classification | $ED_{50}$ (µg/ml) |
| --- | --- |
| Reference Example 1 | 1779.12 |
| Reference Example 2 | 868.95 |
| Example 1 | 760.415 |
| Example 2 | 814.69 |
| Example 3 | 678.93 |

Experimental Example 2. Alkaline Phosphatase Activity (ALP Activity) Measurement In this experimental example, an experiment was carried out to confirm the effect on the alkaline phosphatase activity when treated with the *Gentiana scabra* extract and the *Sambucus williamsii* extract of the present invention by concentration. On the other hand, alkaline phosphatase (ALP; basic phosphatase) is present in most tissues, and ALP present in bone tissue is known to increase its activity when bone growth is actively occurring.

$5×10^3$ MC3T3-L1 cells were seeded into a 6-well plate, and 50 μg/ml ascorbic acid and 10 mM β-glycerophosphate were added to induce differentiation into osteoblasts. After they were treated with each of Reference Examples 1 and 2 and Examples 1 to 3 at concentrations of 50 μg/ml, 100 μg/ml, and 200 μg/ml, and incubated for 48 hours at 37° C. in 5% $CO_2$ incubator, and then washed twice with PBS, and 0.2% triton X-100 was added thereto, and subsequently, lysis was carried out in a 37° C. incubator for 30 minutes. After centrifugation was carried out at 2,500 rpm for 10 minutes, the supernatant was taken to quantify the protein, and 0.1 N glycine and 100 mM p-nitrophenylphosphate (p-NPP) were added to the remaining supernatant and incubated at 37° C. for 30 minutes, and then 0.1 N NaOH was added to stop the reaction, and absorbance was measured at 405 nm to calculate the amount converted to p-nitrophenol by the ALP enzyme. The results are shown in FIG. 1. The NC in FIG. 1 is an experimental group in which nothing was treated as a control group.

Figure 1A:
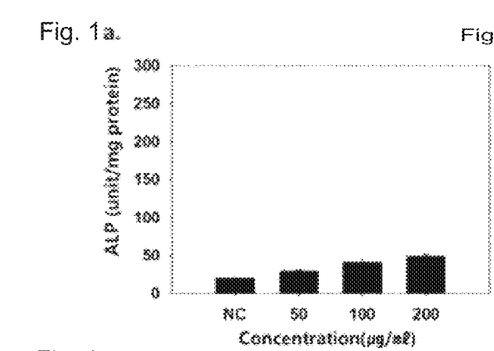
Figure 1B:
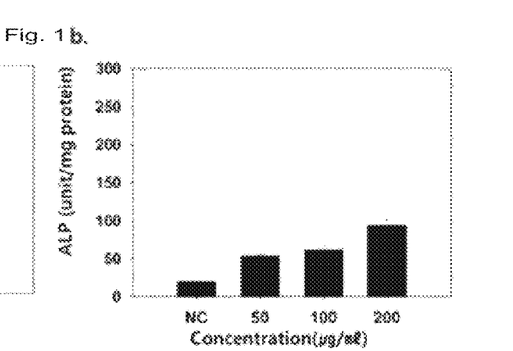
Figure 1C:
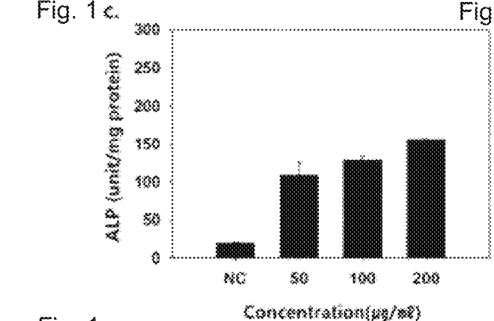
Figure 1D:
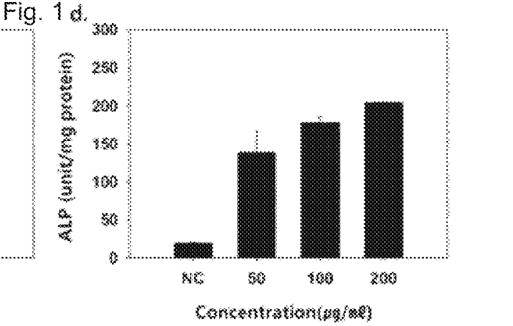
Figure 1E:
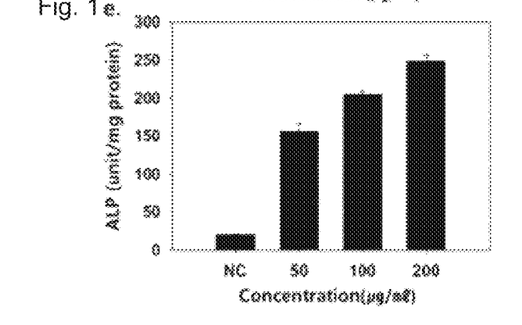

As shown in FIG. 1, it was confirmed that ALP activity increases as the concentration of each extract increases, and it was confirmed that Examples 1 to 3 (FIGS. 1c to 1e) exhibits better ALP activity compared to Reference Example 1 (FIG. 1a) or Reference Example 2 (FIG. 1b). That is, it was confirmed that the ALP activity is remarkably higher when treated with the *Gentiana scabra* extract and the *Sambucus williamsii* extract than when treated with the *Gentiana scabra* extract or the *Sambucus williamsii* extract alone. Accordingly, it was confirmed that the *Gentiana scabra* and the *Sambucus williamsii* of the present invention have excellent bone growth inducing effect.

Experimental Example 3. Tartrate-Resistant Acid Phosphate (TRAP) Measurement

In this experimental example, an experiment was carried out to confirm the effect on the degree of osteoclast differentiation when treated with the *Gentiana scabra* extract and the *Sambucus williamsiis* extract of the present invention by concentration. Specifically, it was confirmed how much they affect the degree of osteoclast differentiation by measuring the increased activity of the TRAP enzyme when osteoclasts act to resorb bone.

On the other hand, the activity of the TRAP enzyme increases when osteoclasts act to resorb bone, and mononuclear osteoclast progenitor cells are formed, and then multinucleated mature osteoclasts in which cells are fused are formed, and adhere to the bone surface. In addition, TRAP exhibits activity in the presence of nitrophenyl phosphate and ATP, and is an osteolytic enzyme that is uniquely present in osteoclasts.

Figure 2:
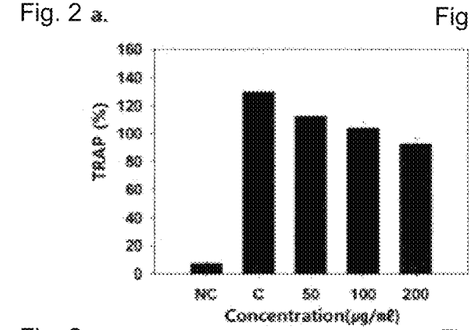

First, $1×10^5$ RAW 264.7 osteoclast precursor cells were seeded into a 6-well plate, and RANKL was put in each well at a concentration of 30 ng/ml, and then osteoblasts treated with each of Reference Examples 1 and 2 and Examples 1 to 3 at concentrations of 50 μg/ml, 100 μg/ml, and 200 μg/ml were treated with a conditioned culture medium and incubated for 3 days. After fixing cells with a mixed solution of citrate-acetone and formaldehyde, 50 mM citrate buffer containing 1.36 mg/mL 4-nitrophenyl phosphate disodium salt and 10 mM tartrate were prepared as a substrate solution, and the substrate solution was into the fixed cells to carry out the reaction for 30 minutes at 37° C. in 5% $CO_2$ incubator, and then the reaction of the enzyme reaction solution was stopped with 0.1 N NaOH, and the optical density was measured three times at a wavelength at 405 nm to obtain the average value and standard deviation, and the results is shown in FIG. 2. The NC in FIG. 2 is an experimental group in which nothing was treated as a control group.

As shown in FIG. 2, it was confirmed that TRAP activity decreases compared to the experimental group in which nothing was treated as the concentration of each extract increases, and it was confirmed that the TRAP enzyme activity with Examples 1 to 3 (FIGS. 2c to 2e) is more remarkably lowered compared to Reference Example 1 (FIG. 2a) or Reference Example 2 (FIG. 2b). That is, it was confirmed that the TRAP enzyme activity is more remarkably lowered when treated with the *Gentiana scabra* extract and the *Sambucus williamsii* extract than when treated with the *Gentiana scabra* extract or the *Sambucus williamsii* extract alone, and thus, it was confirmed that the *Gentiana scabra* extract and the *Sambucus williamsii* extract of the present invention can inhibit bone resorption.

Figure 3:
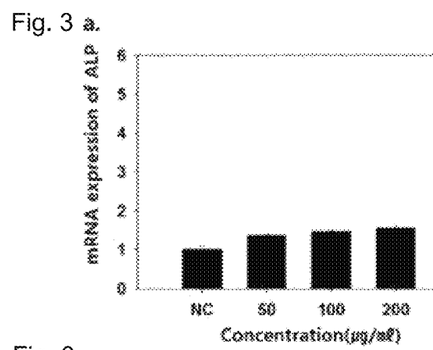
Figure 4:
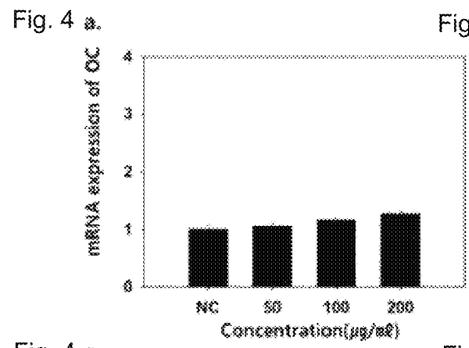

Experimental Example 4. Measurement of Expression of Osteoblast Differentiation-Related Factors in Preosteoblasts Real-time PCR was carried out to confirm whether the osteoblast differentiation-related factors are expressed in the preosteoblasts when treated with the *Gentiana scabra* extract and the *Sambucus williamsii* extract. First, after $1×10^5$ MC3T3-E1 cells were seeded into a 12-well plate, treated with each of Reference Examples 1 and 2 and Examples 1 to 3 at concentrations of 50 μg/ml, 100 μg/ml, and 200 μg/ml, and incubated for 48 hours, and then the cells were recovered and RNA extraction was carried out according to the manufacturer's protocol with the RNeasy extraction kit (Qiagen, Gaithersburg, Md., USA). cDNA was synthesized using the iScript cDNA synthesis kit (Bio-Rad Laboratories Headquarters, Hercules, Calif., USA). To measure the expression of genes, real-time quantitative PCR was carried out using SYBR Green (iQ SYBR Green Supermix, Bio-Rad Bio-Rad Laboratories Inc.), and Real-Time PCR (Applied Biosystems, Foster City, Calif., USA) was used as the device. The base sequences of the genes used for the measurement are shown in Table 3 below. In the real time PCR reaction, 2 μl of cDNA, 10 μl of 2×SYBR mix, and 1 μl of each of 100 pmol/μl forward and reverse primers were added within a total of 20 μl and the rest was filled with $H_2O$. The PCR amplification step was as follows, and the amplification cycle was conducted at 40 cycles. Heating was carried out for 8 minutes at 95° C. for hot start, and then, denaturation at 95° C. for 15 seconds, annealing at 55° C. for 30 seconds, and extension at 72° C. for 30 seconds were repeated in the amplification step and the value was recorded after extension of each cycle. After all cycles were completed, melting curve analysis was carried out to confirm the specificity of the primer. The results were analyzed with One step system software v2.1 provided by Applied Biosystems. The measured results of the expression level of ALP gene are shown in FIG. 3, and the measured results of the expression level of osteocalcin gene are shown in FIG. 4. The NC of FIG. 3 and FIG. 4 above is an experimental group in which no osteoblast differentiation induction experiment was carried out and nothing was treated as a control group.

TABLE 3

| Gene | Primer sequences | SEQ ID NO: |
|---|---|---|
| GAPDH | F 5'-ATGGAAATCCCATCACCATCT-3' | 1 |
|  | R 5'-CGCCCCACTTGATTTTGG-3' | 2 |
| ALP | F 5'-CCGCTTTAACCAGTGCAACA-3' | 3 |
|  | R 5'-CCCGATTCATCACGGAGATG-3' | 4 |
| Osteocalcin | F 5'-CAGGAGGGCAGCGAGGTA-3' | 5 |
|  | R 5'-GCTCCCAGCCATTGATACA-3' | 6 |
| NFATC-1 | F 5'-TGGCCTCCCGCTTATCTCT-3' | 7 |
|  | R 5'-GGATAACGCAGGCGAATTGT-3' | 8 |
| Cathepsin K | F 5'-GATAATGTGAACCATGCAGTGTTG-3' | 9 |
|  | R 5'-CCAGTGCTTGCTTCCCTTCT-3' | 10 |
| MMP-9 | F 5'-ACGCCACGCATTTTCAAAA-3' | 11 |
|  | R 5'-GGCCCATTCCCTCCACAT-3' | 12 |

As shown in FIG. 3, it was confirmed that the expression of ALP gene increases as the concentration of each extract increases, and it was confirmed that Examples 1 to 3 (FIGS. 3c to 3e) exhibits more expression of ALP gene compared to Reference Example 1 (FIG. 3a) or Reference Example 2 (FIG. 3b). That is, it was confirmed that the effect of inducing the expression of ALP gene is superior when treated with the *Gentiana scabra* extract and the *Sambucus williamsii* extract than when treated with the *Gentiana scabra* extract or the *Sambucus williamsii* extract alone. Accordingly, it was confirmed that the *Gentiana scabra* and the *Sambucus williamsii* of the present invention have excellent bone growth inducing effect.

As shown in FIG. 4, it was confirmed that the expression of osteocalcin (OC) increases as the concentration of each extract increases, and it was confirmed that Examples 1 to 3 (FIGS. 4c to 4e) exhibits more expression of osteocalcin compared to Reference Example 1 (FIG. 4a) or Reference Example 2 (FIG. 4b). That is, it was confirmed that the effect of inducing the expression of osteocalcin is superior when treated with the *Gentiana scabra* extract and the *Sambucus williamsii* extract than when treated with the *Gentiana scabra* extract or the *Sambucus williamsii* extract alone. On the other hand, osteocalcin (OC) is a protein that is synthesized by osteoblasts during bone remodeling and is bound to the extracellular matrix of bone, and thus, it was confirmed that the *Gentiana scabra* extract and the *Sambucus williamsii* extract of the present invention can induce bone remodeling.

Experimental Example 5. Measurement of Expression of Osteoclast Differentiation-Related Factors in Preosteoclasts Real-time PCR was carried out to confirm whether the osteoclast differentiation-related factors are expressed in the preosteoclasts when treated with the *Gentiana scabra* extract and the *Sambucus williamsii* extract. $5 \times 10^5$ RAW 246.7 cells were seeded into a 12-well plate, and 10 ng/mL RNAKL and 10 ng/mL M-CSF were added to induce differentiation into osteoclasts. They were treated with each of Reference Examples 1 and 2 and Examples 1 to 3 at concentrations of 50 μg/ml, 100 μg/ml, and 200 μg/ml, and after 48 hours, the cells were recovered and RNA extraction was carried out according to the manufacturer's protocol with the RNeasy extraction kit (Qiagen, Gaithersburg, Md., USA). cDNA was synthesized using the iScript cDNA synthesis kit (Bio-Rad Laboratories Headquarters, Hercules, Calif., USA). To measure the expression of genes, real-time quantitative PCR was carried out using SYBR Green (iQ SYBR Green Supermix, Bio-Rad Bio-Rad Laboratories Inc.), and Real-Time PCR (Applied Biosystems, Foster City, Calif., USA) was used as the device. The base sequences of the genes to be measured are shown in Table 3 above. In the real time PCR reaction, 2 μl of cDNA, 10 μl of 2×SYBR mix, and 1 μl of each of 100 pmol/μl forward and reverse primers were added within a total of 20 μl and the rest was filled with $H_2O$. The PCR amplification step was as follows, and the amplification cycle was conducted at 40 cycles. Heating was carried out for 8 minutes at 95° C. for hot start, and then, denaturation at 95° C. for 15 seconds, annealing at 55° C. for 30 seconds, and extension at 72° C. for 30 seconds were repeated in the amplification step and the value was recorded after extension of each cycle. After all cycles were completed, melting curve analysis was carried out to confirm the specificity of the primer. The results were analyzed with One step system software v2.1 provided by Applied Biosystems.

Figure 5:
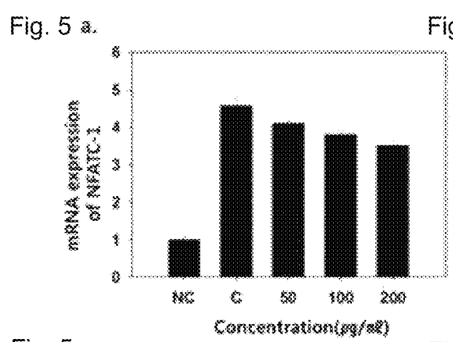
Figure 6:
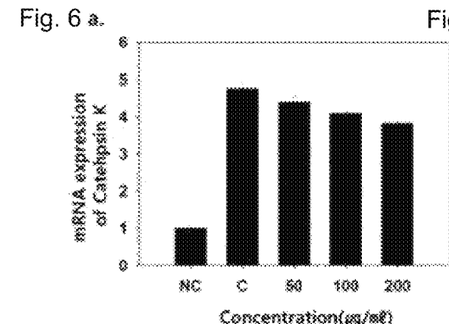
Figure 7:
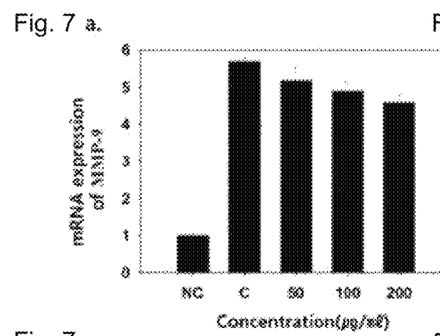

Osteoblast differentiation is initiated by the binding of osteoblasts, a receptor activator of nuclear factor-kb ligand (RANKL), which is an osteoclast inducing factor secreted from activated T lymphocytes, and its receptor RANK expressed in osteoclast progenitor cells. If the binding of RANKL and RANK progresses, the expression of c-fos and NFATC-1 increases, and as a result, the expression of Cathepsin K and MMP9 increases, thereby maintaining the differentiation of osteoclasts. Thus, in Experimental Example 5, the expression level of NFATC-1 gene was measured and the results thereof are shown in FIG. 5, the expression level of Cathepsin K gene was measured and the results thereof are shown in FIG. 6, and the expression level of MMP-9 gene was measured and the results thereof are shown in FIG. 7. The NC of FIG. 5 and FIG. 7 above is an experimental group in which no osteoclast differentiation induction experiment was carried out and nothing was treated as a control group, and the C is an experimental group in which osteoclast differentiation induction experiment was carried out but nothing was treated as a comparative group.

As shown in FIG. 5, it was confirmed that the expression of NFATC-1 gene decreases as the concentration of each extract increases, and it was confirmed that the expression level of NFATC-1 gene with Examples 1 to 3 (FIGS. 5c to 5e) is remarkably lower compared to Reference Example 1 (FIG. 5a) or Reference Example 2 (FIG. 5b). That is, it was confirmed that the effect of inhibiting the expression of NFATC-1 gene is superior when treated with the *Gentiana scabra* extract and the *Sambucus williamsii* extract than when treated with the *Gentiana scabra* extract or the *Sambucus williamsii* extract alone. In particular, as a result treated with Examples 1 to 3 at 200 μg/ml, it was confirmed that the expression of NFATC-1 gene was significantly reduced by 54.96%, 65.10%, and 76.56%, respectively, compared to the experimental group in which nothing was treated after osteoclast differentiation induction.

As shown in FIG. 6, it was confirmed that the expression of Cathepsin K gene decreases as the concentration of each extract increases, and it was confirmed that the expression level of Cathepsin K gene with Examples 1 to 3 (FIGS. 6c to 6e) is remarkably lower compared to Reference Example 1 (FIG. 6a) or Reference Example 2 (FIG. 6b). That is, it was confirmed that the effect of inhibiting the expression of Cathepsin K gene is superior when treated with the *Gentiana scabra* extract and the *Sambucus williamsii* extract than when treated with the *Gentiana scabra* extract or the *Sambucus williamsii* extract alone. In particular, as a result treated with Examples 1 to 3 at 200 μg/ml, it was confirmed that the expression of Cathepsin K gene was significantly reduced by 46.98%, 59.49%, and 74.98%, respectively, compared to the experimental group in which nothing was treated after osteoclast differentiation induction.

As shown in FIG. 7, it was confirmed that the expression of MMP-9 gene decreases as the concentration of each extract increases, and it was confirmed that the expression level of MMP-9 gene with Examples 1 to 3 (FIGS. 7c to 7e) is remarkably lower compared to Reference Example 1 (FIG. 7a) or Reference Example 2 (FIG. 7b). That is, it was confirmed that the effect of inhibiting the expression of MMP-9 gene is superior when treated with the *Gentiana scabra* extract and the *Sambucus williamsii* extract than when treated with the *Gentiana scabra* extract or the *Sambucus williamsii* extract alone. In particular, as a result treated with Examples 1 to 3 at 200 μg/ml, it was confirmed that the expression of MMP-9 gene was significantly reduced by 52.51%, 58.17%, and 72.12%, respectively, compared to the experimental group in which nothing was treated after osteoclast differentiation induction.

As described above, the present invention has been described with reference to the examples shown in the drawings, but these are merely exemplary, and it should be understood that various modifications and equivalent other examples are possible based on common knowledge in the art. Therefore, the true technical protection scope of the present invention is based on the claims to be described below and will have to be determined based on the specific contents of the above-described invention.

The invention claimed is:

1. A method for preventing and/or treating a subject with osteoporosis comprising administering a composition comprising a *Gentiana scabra* extract and a *Sambucus williamsii* extract to the subject,
wherein a weight ratio of the *Gentiana scabra* extract and the *Sambucus williamsii* extract in the composition is 1:0.1 to 10,
wherein the composition comprises the *Gentiana scabra* extract and the *Sambucus williamsii* extract in an amount of 0.001 to 100% by weight, based on a total weight of the composition, and
wherein the *Gentiana scabra* extract and the *Sambucus williamsii* extract are prepared by hot water extraction.

2. The method according to claim 1, wherein the administering the composition to the subject improves expression of a gene related to bone formation in the subject.

3. The method according to claim 2, wherein the gene related to bone formation is one or more gene selected from the group consisting of ALP (alkaline phosphatase), osteocalcin, BMP (bone morphogenetic protein), TGF-β (transforming growth factor-beta), and osteoprotegerin.

4. The method according to claim 1, wherein the administration of the composition to the subject inhibits expression of a gene related to bone resorption in the subject.

5. The method according to claim 4, wherein the gene selected from the group consisting of NF-κB (nuclear factor KappaB), c-FOS, NFATC-1(nuclear factor of activated T cells 1), Cathepsin K, and MMP-9 (matrix metallopeptidase 9).

6. The method according to claim 1, wherein the weight ratio of the *Gentiana scabra* extract and the *Sambucus williamsii* extract in the composition is 1:0.4 to 2.5.

* * * * *